United States Patent [19]

Molinari

[11] Patent Number: 4,845,114
[45] Date of Patent: Jul. 4, 1989

[54] N-(TRANS-P-HYDROXY-CYCLOHEXYL)-(2-AMINO-3,5-DIBROMO)BENZYLAMINE SALTS POSSESSING MUCOLYTIC ACTIVITY

[75] Inventor: Egidio Molinari, Longone al Segrino, Italy

[73] Assignee: Erregierre Industria Chimica Spa, D'Argon, Italy

[21] Appl. No.: 137,348

[22] Filed: Dec. 23, 1987

[30] Foreign Application Priority Data

Jan. 7, 1987 [IT] Italy .................... 19008 A/87

[51] Int. Cl.⁴ ............... C07D 277/06; A01K 31/425; A01K 31/195; C07C 149/43
[52] U.S. Cl. .................... 514/365; 514/554; 548/201; 562/556; 562/557; 558/255
[58] Field of Search ............ 260/501.12; 548/201; 514/365, 554

[56] References Cited
FOREIGN PATENT DOCUMENTS 3425007 1/1985 Fed. Rep. of Germany ...... 544/271

Primary Examiner—Robert Gerstl
Attorney, Agent, or Firm—Arnold, White & Durkee

[57] ABSTRACT

N-(trans-p-hydroxy-cyclohexyl)-(2-amino-3,5-dibromo)benzylamine salts possessing mucolytic activity, and having the general formula:

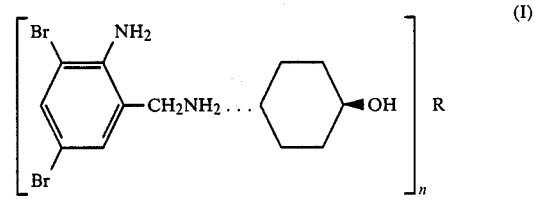

wherein R is the anion of a mono or dicarboxylic amino acid chosen from the group consisting of α-mercaptopropionylglycine, S-benzoyl-α-mercaptopropionylglycine, S-thenoyl-α-mercaptopropionylglycine, acetyl-L-cysteine, carboxymethyl-L-cysteine, thiazolidinemonocarboxylic acid and thiazolidinedicarboxylic acid, and n is 1 if said amino acid is monocarboxylic, n is 1 or 2 if said amino acid is dicarboxylic.

2 Claims, No Drawings

N-(TRANS-P-HYDROXY-CYCLOHEXYL)-(2-AMINO-3,5-DIBROMO)BENZYLAMINE SALTS POSSESSING MUCOLYTIC ACTIVITY

This invention relates to N-(trans-p-hydroxy-cyclohexyl)-(2-amino-3,5-dibromo)benzylamine salts possessing mucolytic activity, the process for their preparation and pharmaceutical compositions which contain them.

More particularly the invention relates to salts of N-(trans-p-hydroxy-cyclohexyl)-(2-amino-3,5-dibromo)benzylamine with mono or dicarboxylic amino acids and having the general formula:

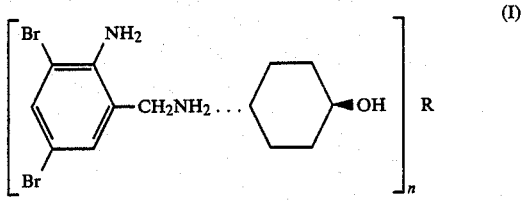

in which R is the anion of a mono or dicarboxylic amino acid chosen from the group consisting of α-mercaptopropionylglycine, S-benzoyl-α-mercaptopropionylglycine, S-thenoyl-α-mercaptopropionylglycine, acetyl-L-cysteine, carboxymethyl-L-cysteine and thiazolidinecarboxylic (thiazolidinemonocarboxylic and thiazolidinedicarboxylic) acid, and n is 1 if said amino acid is monocarboxylic or 1 or 2 if said amino acid is dicarboxylic.

The salts of the invention possess high mucolytic activity associated with very low toxicity and can be used in the treatment of acute and chronic bronchopneumopathies of hypersecretory type, in which they exert a therapeutically useful expectorant activity.

The present invention also relates to pharmaceutical compositions characterized by containing as active principle an effective quantity of one or more compounds of formula (I), either as such or in mixture with pharmaceutically acceptable vehicles, diluents, solvents and/or excipients.

Finally, the invention also relates to the process for preparing salts of general formula (I), characterized by reacting N-(trans-p-hydroxy-cyclohexyl)-(2-amino-3,5-dibromo)benzylamine with an amino acid in a reaction medium consisting of an organic solvent or a mixture of organic solvents, in which said reagents are soluble and from which the salt obtained separates by precipitation.

These and further characteristics of the salts according to the present invention and of the process of their preparation will be more apparent from the description given hereinafter which relates to preferred methods of preparing the salts and to preferred pharmaceutical compositions, and is given for illustrative purposes only.

The salts of general formula (I) according to the present invention are prepared by reacting one mole of amino acid with one mole of N-(trans-p-hydroxy-cyclohexyl)-(2-amino-3,5-dibromo)benzylamine or with two moles of this benzylamine if said amino acid is of dicarboxylic type and the neutral salt is required.

Said amino acid, which can be of monocarboxylic or dicarboxylic type, is chosen from the group consisting of α-mercaptopropionylglycine, S-benzoyl-α-mercaptopropionylglycine, S-thenoyl-α-mercaptopropionylglycine, acetyl-L-cysteine, carboxymethyl-L-cysteine, thiazoldinedicarboxylic acid and thiazolidinedicarboxylic acid.

The reaction medium is preferably ethyl acetate, but other solvents can be used such as methanol or ethanol, or mixtures of ethyl acetate with these, or other types of mixtures.

The N-(trans-p-hydroxy-cyclohexyl)-(2-amino-3,5-dibromo)benzylamine is slightly heated in the solvent until it has completely dissolved, after which the amino acid solution is added.

The reaction is conducted at ambient temperature under agitation.

The salt of general formula (I) which forms from the reaction separates in the form of a white crystalline powder.

The salts according to the invention possess very useful expectorant characteristics in therapeutic applications, and are completely reliable because of their very low toxicity.

Because of these properties said salts are particularly useful as active principles in pharmaceutical compositions, both as such and in mixture with pharmaceutically acceptable vehicles, diluents, solvents and/or excipients.

Said pharmaceutical compositions can be in solid form, such as capsules, tablets, pills and suppositories, or in liquid form such as ready or extemporaneous solutions, ready or extemporaneous emulsions, spray preparations or ready or extemporaneous injectable solutions either for intramuscular or intravenous use.

These compositions can be prepared following the methods and using vehicles, solvents, diluents and/or excipients which are well known to the expert of the art, and are fully described for example in the book "Tacnologia farmaceutica" by S. Casadio, published by Cisalpina Goliardica-Milan 1972.

The following examples of the preparation of salts of general formula (I) are described for non-limiting illustration only.

EXAMPLE 1

Preparation of the α-mercaptopropionylglycine salt:

76 g of N-(trans-p-hydroxy-cyclohexyl)-(2-amino-3,5-dibromo)benzylamine are dissolved in 200 ml of ethyl acetate by heating slightly until completely dissolved. 33 g of α-mercaptopropionyl glycine dissolved in 350 ml of ethyl acetate are added to the solution obtained. On standing at room temperature the salt which forms separates as a white crystalline powder of M.P. 199.5°–201.5° C.

On analysis for $C_{13}H_{18}Br_2N_2O \cdot C_5H_9NO_3S$ the following are found: $C_{13}H_{18}Br_2N_2O$: calculated 69.85%, found 69.6%. $C_5H_9NO_2S$: calculated 30.15%, found 30.2%.

EXAMPLE 2

Preparation of the acetyl-L-cysteine:

38 g of N-(trans-p-hydroxy-cyclohexyl)-(2-amino-3,5-dibromo)benzylamine are dissolved in 200 ml of ethyl acetate by heating slightly until completely dissolved. 16 g of acetyl-L-cysteine dissolved in 50 ml of methanol are added to the solution obtained. The salt which forms precipitates as a white crystalline powder of M.P. 138.5°–140.5° C.

On analysis for $C_{13}H_{18}Br_2N_2O \cdot C_5H_9NO_3S$ the following is found: $C_{13}H_{18}Br_2N_2O$: calculated 69.85%, found 69.8%.

EXAMPLES 3 to 6

Operating as described in the preceding examples and reacting the following amino acids individually with N-(trans-p-hydroxycyclohexyl)-(2-amino-3,5-dibromo)-benzylamine: S-thenoyl-α-mercaptopropionylglycine, S-benzoyl-α-mercaptopropionylglycine and thiazolidinedicarboxylic acid in a molar ratio of 1/1 with respect to said benzylamine, and thiazolidinedicarboxylic acid in a molar ratio of 0.5/1 with respect to said benzylamine, the following salts were obtained having the reported characteristics:

S-thenoyl-α-mercaptopropionylglycine salt: white crystalline powder, M.P. 144°–150.5° C.; analysis for $C_{13}H_{18}Br_2N_2O \cdot C_{10}H_{11}NO_4S_2$: $C_{13}H_{18}Br_2N_2O$: calculated 58.04%, found 58.0%;

S-benzoyl-α-mercaptopropionylglycine salt: white crystalline powder; M.P. 130°–133° C.; analysis for $C_{13}H_{18}Br_2N_2O \cdot C_{12}H_{13}NO_4S$: $C_{13}H_{18}Br_2N_2O$: calculated 58.58%, found 58.62%;

acid salt of thiazolidinedicarboxylic acid: white crystalline powder; analysis for $C_{13}H_{18}Br_2N_2O \cdot C_5H_7NO_4S$: $C_5H_7NO_4S$: calculated 31.9%, found 31.3%;

neutral salt of thiazolidinedicarboxylic acid: white crystalline powder, M.P. 174°–178° C.; analysis for $(C_{13}H_{18}Br_2N_2O)_2 \cdot C_5H_9NO_4S$: $C_5H_9NO_4S$: calculated 18.9%, found 18.6%.

I claim:

1. A salt of N-(trans-p-hydroxycyclohexyl)-(2-amino-3,5-didromo)benzylamine with a mono or dicarboxylic amino acid, the salt having the following formula:

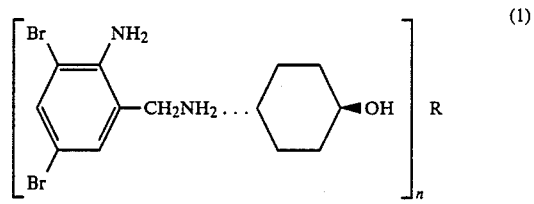

wherein R is the anion of a mono or dicarboxylic amino acid chosen from the group consisting of α-mercaptopropionylglycine, S-benzoyl-α-mercaptopropionylglycine, S-thenoyl-α-mercaptopropionylglycine, acetyl-L-cysteine, carboxymethyl-L-cysteine, thiazolidinemonocarboxylic acid and thiazolidinedicarboxylic acid, and n is 1 if said amino acid is monocarboxylic, n is 1 or 2 if said amino acid is dicarboxylic.

2. A pharmaceutical composition comprising a mucolitic and expectorant effective quantity of one or more compounds of the formula

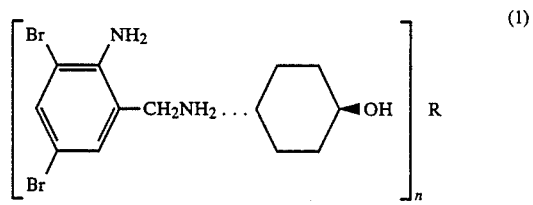

wherein R is the anion of a mono or dicarboxylic amino acid chosen from the group consisting of α-mercaptopropionylglycine, S-benzoyl-α-mercaptopropionylglycine, S-thenoyl-α-mercaptopropionylglycine, acetyl-L-cysteine, carboxymethyl-L-cysteine, thiazolidinemonocarboxylic acid and thiazolidinecarboxylic acid, and n is 1 if said amino acid is monocarboxylic, n is 1 or 2 if said amino acid is dicarboxylic, either as such or in mixture with one or more pharmaceutically acceptable vehicle, diluent, solvent and/or excipient.

* * * * *